(12) United States Patent
Pruett et al.

(10) Patent No.: US 9,075,028 B2
(45) Date of Patent: Jul. 7, 2015

(54) AIRBORNE SUBSTANCE DETECTOR (75) Inventors: James A. Pruett, Allen, TX (US);
Jeffery L. Williams, Auburn, IN (US);
Gary Schwartz, Dallas, TX (US)

(73) Assignee: Raytheon Company, Waltham, MA (US)

( * ) Notice: Subject to any disclaimer, the term of this patent is extended or adjusted under 35 U.S.C. 154(b) by 378 days.

(21) Appl. No.: 13/596,217

(22) Filed: Aug. 28, 2012

(65) Prior Publication Data

US 2014/0298890 A1 Oct. 9, 2014

(51) Int. Cl.
*G01N 7/00* (2006.01)
*G01N 33/00* (2006.01)
*G01N 1/22* (2006.01)
*G01N 1/24* (2006.01)
*G01N 1/02* (2006.01)

(52) U.S. Cl.
CPC .......... *G01N 33/0004* (2013.01); *G01N 1/2273* (2013.01); *G01N 2001/245* (2013.01); *G01N 2001/024* (2013.01)

(58) Field of Classification Search
CPC .... G01N 33/0004; G01N 1/2273; G01N 1/24
USPC ...................... 73/31.02, 31.03, 28.01, 864.32
See application file for complete search history.

(56) References Cited

U.S. PATENT DOCUMENTS

| 4,358,909 | A  | * | 11/1982 | Trikilis ............................. 49/42 |
| 7,383,719 | B1 |   | 6/2008  | Pellegrino et al. |
| 7,594,422 | B2 | * | 9/2009  | Perry et al. ..................... 73/1.02 |
| 7,666,356 | B2 |   | 2/2010  | O'Donnell et al. |
| 8,307,723 | B2 | * | 11/2012 | Novosselov et al. ....... 73/864.32 |
| 2003/0132279 | A1 | * | 7/2003 | Stemmle .......................... 232/31 |
| 2011/0024626 | A1 | * | 2/2011 | O'Donnell et al. ......... 250/338.1 |
| 2011/0132108 | A1 | * | 6/2011 | Novosselov et al. ....... 73/863.22 |

* cited by examiner

*Primary Examiner* — Hezron E Williams
*Assistant Examiner* — Tarun Sinha
(74) *Attorney, Agent, or Firm* — Renner, Otto, Boisselle & Sklar, LLP (57) ABSTRACT

An airborne substance detector includes an air intake that sweeps through a fixed area, and a fan that draws air toward an effluence detection device that analyzes the air for one or more substances, such as explosives. The air intake may be a series of tubes of a rotary gate, with multiple sets of tubes that rotate about a central axis. The fan or blower draws air through holes in the tubes, and through a manifold that directs air to the effluence detection device from a single set of tubes at a time. In addition the detector may include a heater that may enhance vaporization of substances to be detected. The effluence detection device, the manifold, and the fan may be located in an enclosure at the top of the rotary gate. After detection, a decontamination procedure may be initiated to purge the system of the substance that was detected.

18 Claims, 7 Drawing Sheets

AIRBORNE SUBSTANCE DETECTOR

BACKGROUND OF THE INVENTION

1. Field of the Invention

The invention is in the field of airborne substance detectors.

2. Description of the Related Art

Increased concern about terrorism has brought to the fore the need to screen personnel entering public areas and other sensitive spaces where attacks might occur. Screening people for chemicals, such as traces of explosives, is a time-consuming process, making it impractical to be applied for screening large numbers of people rapidly. In addition, current screening methods generally provide notice to those screened of the occurrence of screening. It would be desirable to have screening that was discrete, cost-effective, did not unduly slow movement of people, and successful in finding the desired substances (which may include contraband such as illegal drugs).

SUMMARY OF THE INVENTION

According to various aspects of the invention, an airborne substance detector includes: an air intake that moves through a fixed area, wherein the air intake has holes; a fan; and an effluence detection device that analyzes for one or more airborne substances; wherein the fan draws air through the holes and toward the effluence detection device. The airborne substance detector may optionally include one or more of the following features (in any combination of compatible features): the air intake includes one or more tubes, with air intake holes in at least some of the one or more tubes; the one or more tubes include horizontal tubes; the one or more tubes rotate about a central post of the detector; the one or more tubes are parts of a rotary gate that allows pass through of persons in only one direction; the one or more tubes are in multiple sets of tubes that are circumferentially spaced about the central post; the one or more tubes include horizontal tubes; the horizontal tubes are attached to vertical tubes in the central post; at least some of the one or more tubes have rough surfaces; at least some of the one or more tubes have porous surfaces; the detector includes a rotary gate; at least part of the air intake is on a turnstile of the rotary gate; and the part of the air intake sweeps through the fixed area as the turnstile turns; the air intake is coupled to a manifold that selectively draws in the air through different parts of the air intake; the detector may include a filter; the fan draws air through the air intake along an air flow path; the filter rotates through the air flow path; the filter also passes the sample to the effluence detection device as the filter rotates; the effluence detection device is configured to detect explosives or other substances of interest; the effluence detection device may be configured for detecting illegal narcotic substances; the fan is in a flow loop that includes a heater for heating air that passes through the flow loop; the flow loop includes fittings with respective plugs that can be moved to reconfigure the flow loop; the flow loop can be reconfigured to use the fan and the heater for decontamination of the airborne substance detector after the one or more substances are detected; the detector includes a fixed shield that shields the fixed area from wind or other air currents; the shield includes a curved sheet, possibility made of plastic or metal; the detector includes a space heater directed at part of the fixed area; the space heater includes an infrared heater; the detector may include one or more cameras; the cameras include one or more video cameras; the filter is in a filter housing; the effluence detection device is placed over a port in the filter housing; the filter is continuously rotated while the detector is in normal operation; the filter is rotated among indexed positions while the detector is in normal operation; the filter is rotated at at least 20 revolutions per minute; the filter is on a frame; the filter and the frame are rotated by a motor; the manifold is stationary relative to the turnstile; the manifold is stationary relative to rotating parts of the rotary gate; one or more components of the detector are within a top container that is above the fixed area; the top container is above the turnstile; the top container contains the filter; the top container contains a filter housing that is around the filter; the top container contains the flow loop; the top container contains the fan or blower; the top container contains the one or more cameras; the top container is cylindrical; the top container hides its contents from view; different of the air intake holes are of different sizes; holes between the horizontal tubes and the vertical tubes may have different sizes; the space heater may be aimed at a persons passing through the detector; the manifold has a curved slot; the manifold allows air flow through one of the vertical tubes toward the sniffer, while blocking flow through other of the vertical tubes.

According to other aspects of the invention, a method of airborne detection of one or more substances includes: detecting the one or more substances using the airborne detector having any combination of features of the previous paragraph, as a person passes through a fixed area.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

The annexed drawings, which are not necessarily to scale, show various aspects of the invention.

DETAILED DESCRIPTION

An airborne substance detector includes an air intake that sweeps through a fixed area, and a fan or blower that draws air toward a effluence detection device that analyzes the air for one or more substances, such as explosives. The air intake may be a series of tubes of a rotary gate, with multiple sets of tubes that rotate about a central axis as people pass through the gate, one at a time. The fan or blower draws air through holes in the tubes, and through a manifold that directs air to the effluence detection device. In addition the detector may include a heater that may enhance vaporization of substances to be detected. The effluence detection device, the manifold, and the fan may be located in an enclosure at the top of the rotary gate. Detection of a substance by the effluence detection device may trigger an alarm or send a discrete signal to warn security personnel. After detection, a decontamination procedure may be initiated to purge the system of the substance that was detected.

Figure 1:
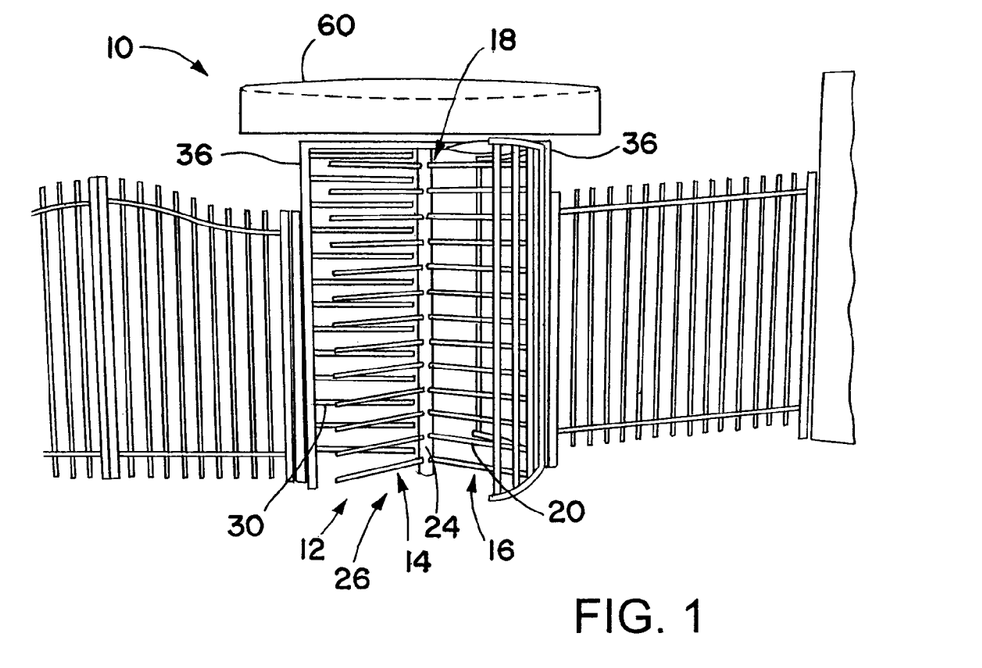
FIG. 1 is an oblique view of an airborne substance detector according to an embodiment of the present invention.

FIG. 1 shows an airborne substance detector 10 that is in the form of and includes a rotary gate 12. Such gates are used at the entryways to all sorts of places and events, such as sporting events, political rallies and conventions, schools, and other places where the public gathers, or to otherwise control passage by individuals on foot, from one public area to another, or from a public area to a restricted or sensitive area, such as the passage onto a military base. The rotary gate 12 includes multiple sets 14, 16, and 18 of horizontal tubes 20 that are attached to a rotating central post 24. The hollows tubes 20 may have cross-sections that may be circular, square, rectangular, or other shapes. The tubes 20 may have smooth inner surfaces. The tubes 20 and the central post 24 together constitute a turnstile 26. The turnstile 26 may be configured to rotate in one direction only, with horizontal tubes 30 constituting a fixed tube set 32 that are fixedly secured to a fixed frame 36 that the turnstile 26 rotates within. The horizontal tubes 30 are mounted at heights such that the tubes 20 of the sets 14-16 pass in between the tubes 30, as the turnstile 26 is turned.

Figure 2:
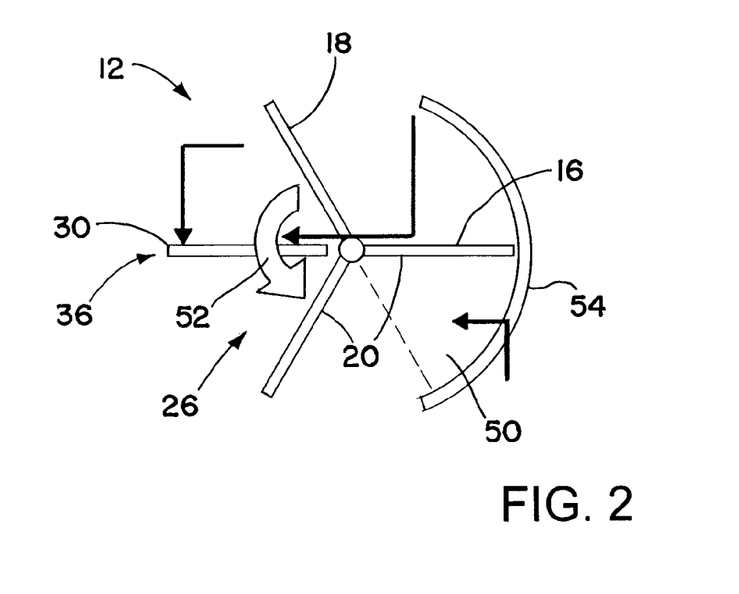
FIG. 2 is a plan view schematically illustrating operation of a rotary gate of the airborne substance detector of FIG. 1.

The frame 36 controls access to the rotary gate 12, and directs foot traffic through the rotary gate 12. Referring now in addition to FIG. 2, a fixed area 50 is defined within the frame 36. A person passes through the fixed area 50 as he or she goes through the rotary gate 12. To pass through the rotary gate 12 the person passes through the fixed area 50 while the turnstile 26 rotates in direction 52. The turnstile 26 is rotated by the person as he or she passes through the gate 12, although alternatively the turnstile 26 may be driven externally. Thus the tubes 20 also pass through the fixed area 50 as part of the normal operation of the rotary gate 12, with one of the tube sets 14-18 passing through the fixed area 50 immediately after each person passes through the fixed area 50.

A person passing through the fixed area (sample collection area) 50 may leave chemical traces in the air that it may be advantageous to detect. For example, handling of explosives may leave residues of the explosive on a person, residues which produce, in the air around the person, detectable traces of volatile compounds in the explosive material. Possession of explosives or an explosive device may produce similar chemical traces in the surrounding air. Other chemicals, such as illegal drugs, may also produce volatile compounds that are detectable in the air. The purpose of the detector 10 is to enable detection of one or more substances, such as explosives or illegal drugs, as a person passes through the fixed area within the gate 12.

Shielding 54 on the frame 36 may aid in preventing wind or other external air currents from disturbing the air in the fixed area 50. The shielding 54 may be curved plastic sheeting, such as clear plastic sheeting or opaque plastic sheeting, or alternatively may be made of another suitable material, such as metal.

The airborne substance detector 10 includes a container 60 (FIG. 1) at its top, where operative parts are located for drawing air in, and for analyzing the air for the presence of one or more substances. The detector 10 also includes components for communicating a positive test (detection of the presence of the one or more substances), and for purging the system after a positive test.

Some or all of the tubes 20 may have roughened and/or porous surfaces 62 that may enhance separation of substances from the hands or other parts of the person. For example, roughness on the tubes at hand level may enhance separation and vaporization of substances such as those that the airborne substance detector 10 is configured to detect. Placing porous material on some or all of the tubes 20 may also enhance separation of detectable substances from the hands, other body parts, or clothing of a person passing through the rotary gate 12.

Figure 3:
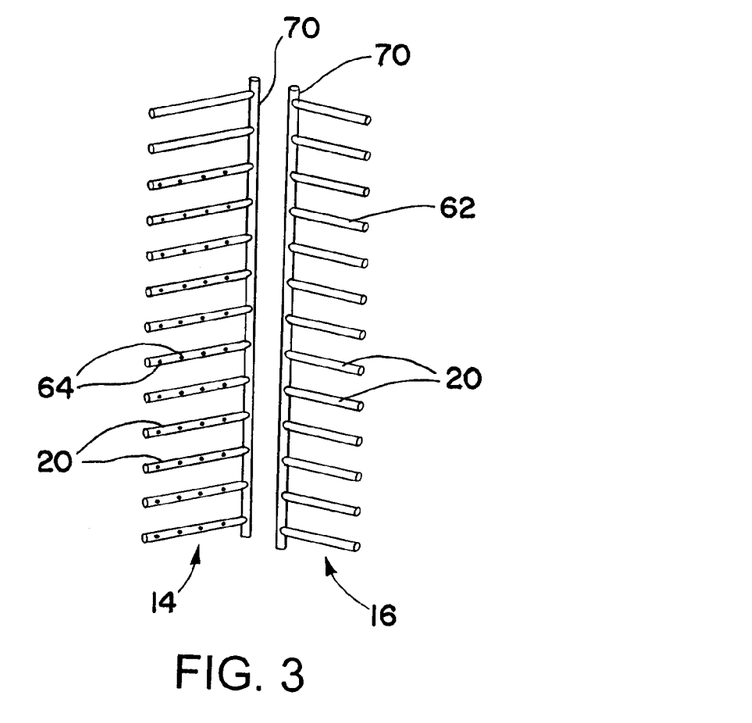
FIG. 3 is an oblique view of some of the tubes of the airborne substance detector of FIG. 1.

FIG. 3 shows air intake holes 64 in the tubes 20 that are air intakes for bringing air in to be analyzed. The air intake holes 64 may be located and sized to bring in desired amounts of air from different locations within the fixed area 50 (FIG. 2). For example, the air intake holes 64 may be located on the leading edges of some or all of the tubes 20, the sides of the tubes 20 that first encounter the fixed area 50. The air intake holes 64 may be omitted from the tubes 20 that are above or below likely head or chest level of persons using the gate 12. In addition, the number, size, and/or placement of holes may be different for tubes 20 at different heights. Further, the size and/or spacing of the air intake holes 64 may change along the length of an individual tube 20. Additional air intake holes may be located on some or all of the horizontal tubes 20 other than at their leading edges.

Figure 4:
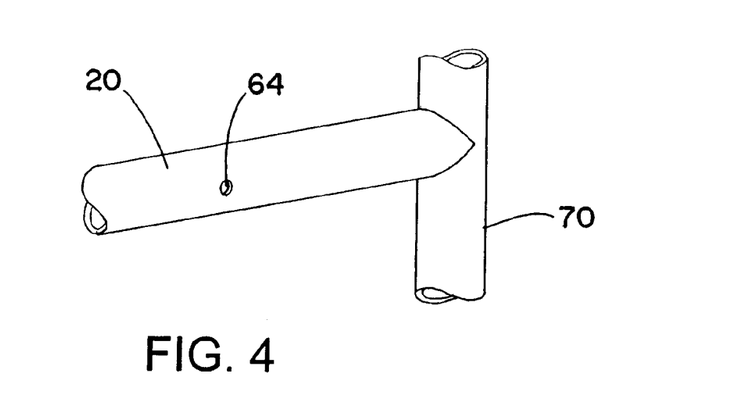
FIG. 4 is an oblique view illustrating connection between a horizontal tube and a vertical tube, some of the tubes of FIG. 3.
Figure 5:
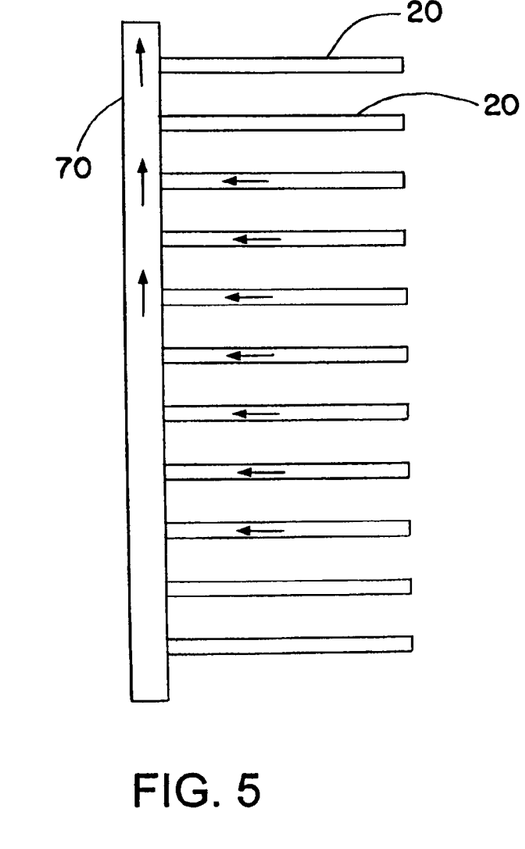
FIG. 5 is a side schematic view illustrating air flow through some of the tubes of the airborne substance detector of FIG. 1.

FIG. 4 shows a connection from one of the horizontal tubes 20 to a vertical tube 70 that supports the horizontal tubes 20 of one of the sets of the horizontal tubes 20. Air flows unhindered from the horizontal tube 20 to the vertical tube 70. The overall air flow in the tubes 20 and 70 is illustrated in FIG. 5. Alternatively there may be a flow hole that limits air flow from the horizontal tube 20 to the vertical tube 70.

Figure 6:
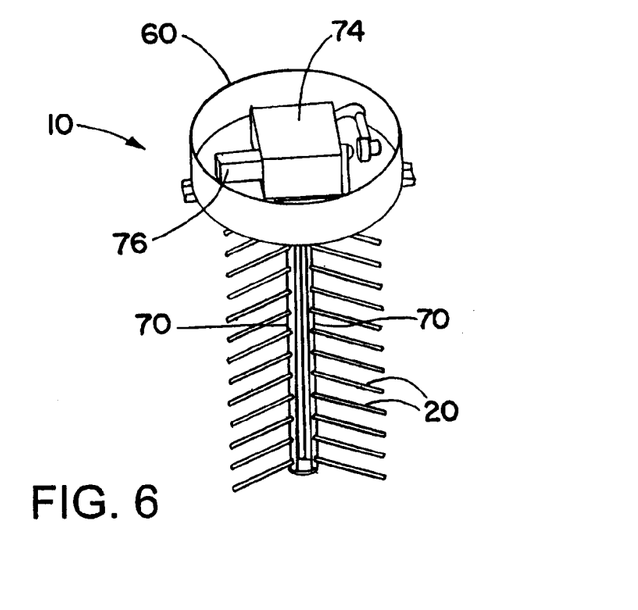
FIG. 6 is an oblique view of some of the components of the airborne substance detector of FIG. 1, illustrating the overall layout of some of the components of the top container.

FIG. 6 shows the general layout of in the top container 60 at the top of the airborne substance detector 10. Air is taken in through the horizontal tubes 20, passes up through the vertical tubes 70 and into a filter assembly 74. An effluence detection device 76 is attached to the filter assembly 74 to analyze the air pulled through tubes 20 and 70.

Figures 7, 8:
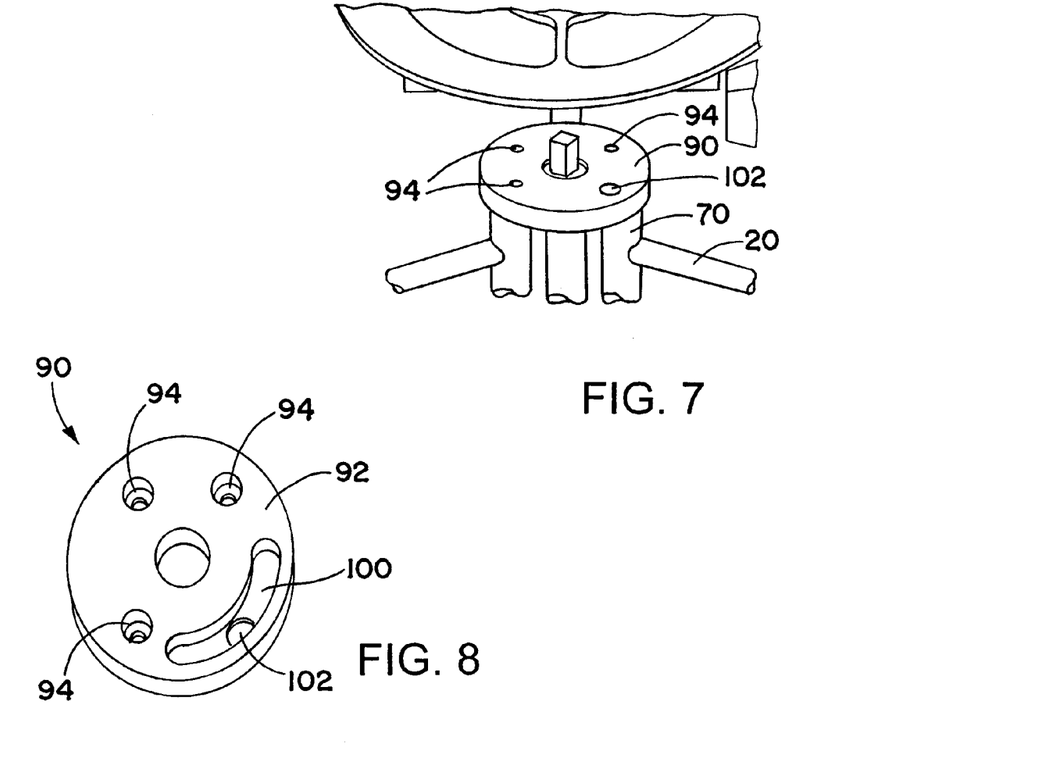
FIG. 7 is an oblique showing a manifold relative to other components of the airborne substance detector of FIG. 1.
FIG. 8 is an oblique view showing the underside of the manifold of FIG. 7.
Figure 9:
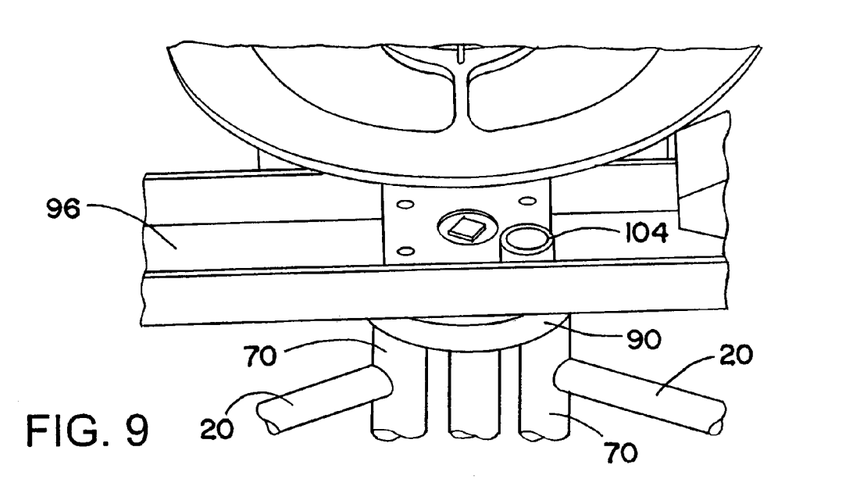
FIG. 9 is an oblique view showing the manifold secured to a fixed beam of the airborne substance detector of FIG. 1.

Making reference now to FIGS. 7-9, a manifold 90 is used to control flow from the open tops of the vertical tubes 70. The manifold 90 directs incoming air from one of the vertical tubes 70 at a time. This allows preferential sampling from the fixed area 50 (FIG. 2), the region of most interest, where the people passing through the gate 12 (FIG. 1) pass one at a time. FIG. 7 shows the manifold 90 at the top of the vertical tubes 70, between the tubes 70 and the top container 60 (FIG. 6). The manifold 90 stays in place as the turnstile 26 (FIG. 1) rotates, directing flow from different of the vertical tubes 70, in turn, to the filter assembly 74 (FIG. 6) and the sniffer 76 (FIG. 6).

FIG. 8 shows an underside 92 of the manifold 90. The manifold 90 has three attachment holes 94 for receiving bolts or other suitable fasteners (not shown) for attaching the manifold 90 to a fixed beam 96, shown in FIG. 9. The manifold underside 92 also has a circumferential curved slot 100 that is in communication with an exit hole 102 on the top of the manifold 90. The curved slot 100 covers an arc that corresponds to the angle that a single of set of the tubes 20 covers as they pass through the fixed area 50 (FIG. 2). In the illustrated embodiment the curved slot 100 covers an arc of 90 degrees, although alternatively the arc may cover any of a broad range of other angles, for example 30 to 180 degrees. As the turnstile 26 (FIG. 1) rotates different of the vertical tubes 70 pass into engagement (fluid communication) with the curved slot 100, allowing air to be pulled into the filter assembly 74 through different of the sets of the horizontal tubes 20. Air entering into the curved slot 100 exits the manifold 90 through the exit hole 102, and then through a fitting 104 in the beam 96.

Figure 10:
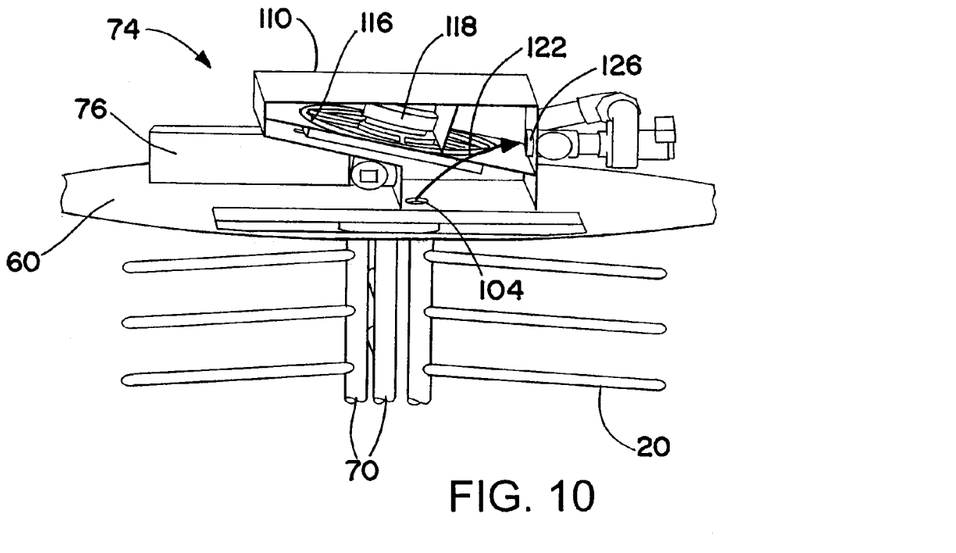
FIG. 10 is an oblique view of components of the top container of FIG. 6, with an access door of the filter assembly housing removed for illustration purposes.
Figure 11:
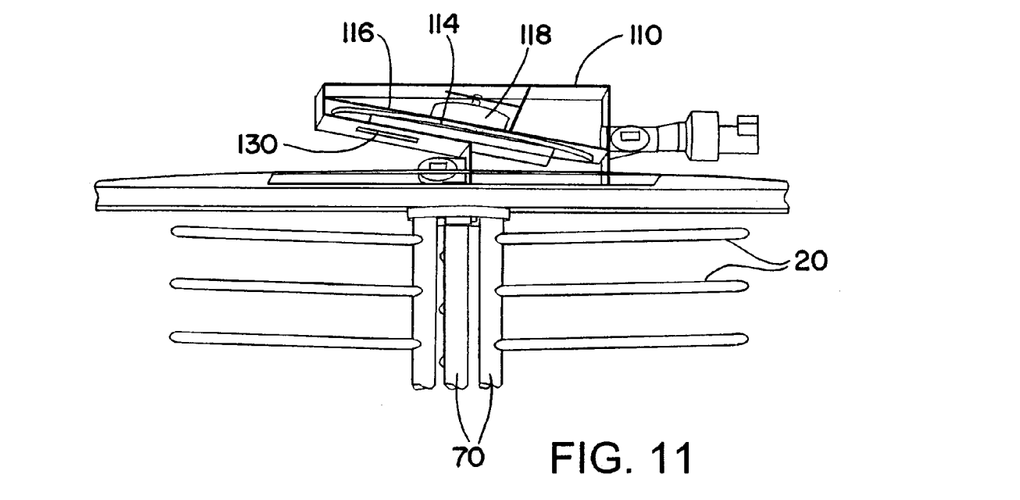
FIG. 11 is another oblique view of the components of FIG. 10, with the sniffer omitted in order to show the effluence detection port of the filter assembly housing.

From the fitting 104 the air enters a housing 110 of the filter assembly 74, shown in FIGS. 10 and 11. A filter 114 within the housing 110 rotates during operation. The filter 114 may be made of a stainless steel mesh, or made be made of another suitable material. The filter 114 is attached to a frame 116 which in turn is attached to a motor 118 that rotates the frame 116 and the filter 114. As the filter 114 rotates it passes through an air flow path 122 from the entry at the fitting 104 to an air flow port 126 at one side of the housing 110. Further in its rotation the filter 114 passes over a sniff port 130, over which the sniffer 76 is attached to the housing 110. The sniffer 76 is able to detect substances in the filter 114, trapped there when the filter 114 passed through the air flow path 122, as the filter 114 moves past the sniffer 76 (at the sniffer port 130). An example of a suitable effluence detection device is the Quantum Sniffer QS-H150 Portable Hand-held Explosives Trace Detector, available Implant Sciences Corporation, of Wilmington, Mass. Another example is the Real Time Atmospheric Pressure Mobility Spectrometer (RTAPMS), available from Raytheon Company, Tucson, Ariz. A further example is MOBILETRACE, available from Morpho Detection, Incorporated of Newark, Calif. Many different configurations are possible. For instance, the effluence detection device alternatively might be too large to fit in the top container 60, and might be located elsewhere, such as on the ground beside the gate 12.

The filter 114 may be rotated about its axis at a rate of 20 revolutions per minute (rpm), for example corresponding to a time of 3 seconds for each person to pass through the rotary gate 12. The filter 114 may rotate at another speed, such as 40 to 60 rpm, or any of a variety of other suitable rates. As an alternative to continuous rotation, the filter 114 may be rotated by steps, using a stepper motor. Stepped rotation of the filter 114 may be coordinated with rotation of the turnstile 26 (FIG. 1).

Figure 12:
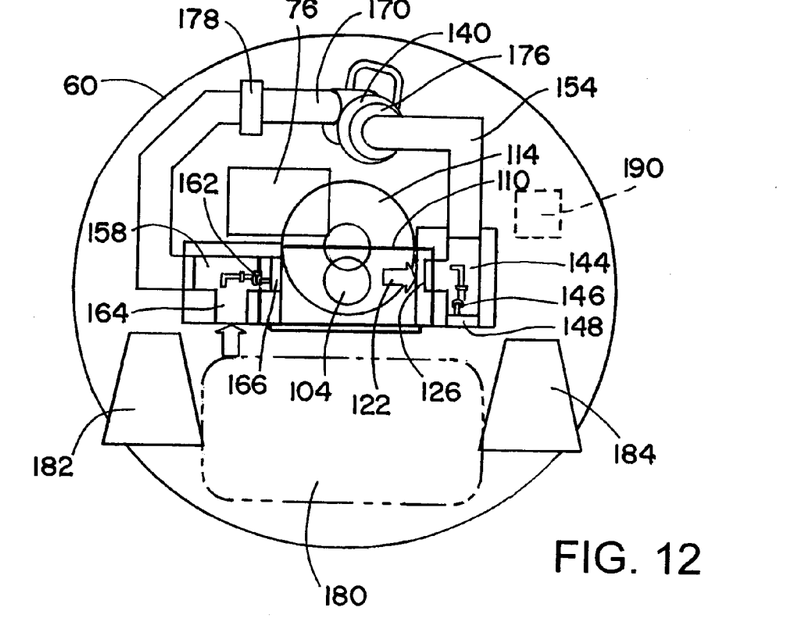
FIG. 12 is a plan view showing components of the top container, with the components configured for normal operation.

FIG. 12 shows further details of the plumbing within the top container 60. A blower or fan 140 pulls flow through the filter assembly housing 110 along the flow path 122, from the entry at the fitting 104 to exit at the port 126. The port 126 is part of a tee fitting 144. The tee fitting 144 has another port 146 that can be connected with the environment outside of the filter assembly housing 110. In normal operation a plug 148 is placed in the port 146, which allows flow to be pulled from the filter assembly housing 110 into a flow loop 154, as has been described above. In the loop 154 the flow passes through the blower or fan 140. A second tee fitting 158 is downstream of the blower 140. One output port 162 of the tee fitting 158 is able to direct flow from the loop 154 outside of the filter housing 110, while another output port 164 is available for directing flow from the loop 154 into the filter housing 110. In normal operation a plug 166 is placed in the output port 164 to block flow through it.

As an alternative to the tee fittings 144 and 158 and the plugs 148 and 166, one or more valves may be used. The valves may be manually-operated valves and/or solenoid-operated valves.

A heater 170 is also in the flow loop 154. The heater 170 is used for decontamination of the system, as described further below. In the illustrated embodiment the heater 170 is immediately downstream of the blower or fan 140. Alternatively the heater 170 may be located elsewhere in the loop 154. The blower 140 and the heater 170 are coupled to adjacent tubing sections 172 and 174 with quick-disconnect fittings 176 and 178, to allow the blower 140 and/or the heater 170 to be easily swapped.

The top container 60 also may have other features shown in FIG. 12. An access door 180 may be used for obtaining access to the container 60. An alarm 182 may be used to signal detection of one or more airborne substances that the effluence detection device 76 is configured to detect. The alarm 182 may signal detection in any of a variety of ways, including a visual or auditory signal, or a radio or infrared signal to a remote station. The alarm signal may or may not be visible or evident to some or all of those in the vicinity of the rotary gate 12 (FIG. 1). For example the alarm may be a silent alarm sent to a monitoring station, perhaps in the vicinity of the rotary gate 12. Detection by the effluence detection device 76 may also trigger one or more changes in operation of the rotary gate 12, for example activating a camera 184 used for taking video or photographs as users pass through the rotary gate 12, or for locking the turnstile 26 (FIG. 1) to prevent further operation of rotary gate 12 until the system can be decontaminated. Alternatively the camera 184 may be in continuous operation, with the alarm 182 optionally triggering retention of images for later use as evidence, for example.

An infrared or other space heater 190 may be located on an underside of the top container 60. The space heater 190 may be directed toward the fixed area 50 (FIG. 1) and/or an adjoining area within the rotary gate 12 (FIG. 1). An example of a suitable heater is any of a series of infrared heaters available from McMaster-Carr, of Elmhurst, Ill. By heating the area where individual users of the rotary gate 12 pass, volatilization of explosive traces (or other substances) may be enhanced, facilitating detection of such substances. The heating from the space heater 190 may be directed at a selected height, for example at the expected height of the chest or hands of users of the rotary gate 12. The space heater 190 may be located elsewhere on the detector 10 (FIG. 1), such as on a side of the gate 12. As another alternative multiple space heaters may be used. The heater(s) 190 may be configured to heat a person as he or she passes through the rotary gate 12, rather than the air within the rotary gate 12. Since exposure to the heater(s) 190 is brief, a person passing through the rotary gate 12 is unlikely to be aware that his or her outerwear has been energized. The space heater(s) 190 may be omitted entirely, if desired.

Figure 13:
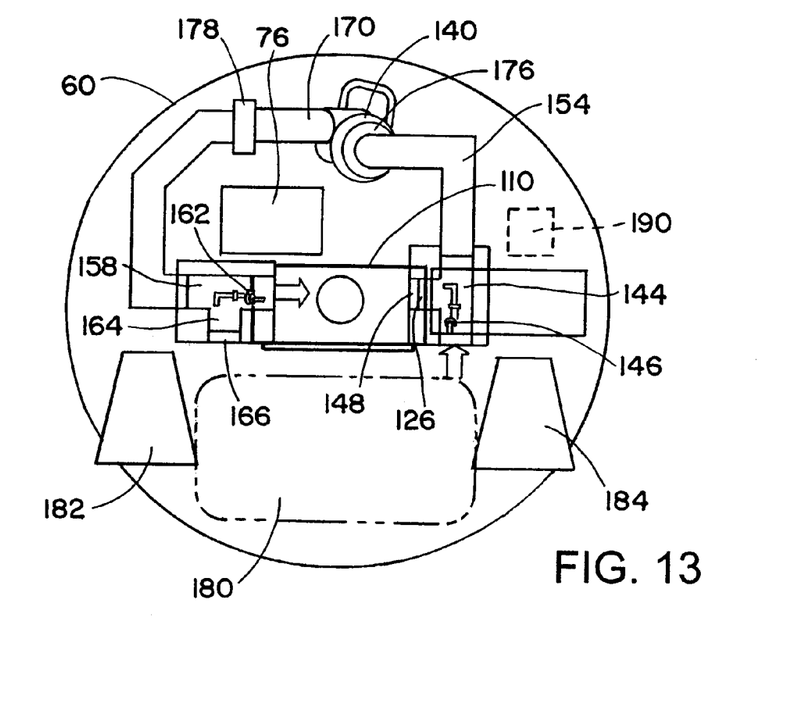
FIG. 13 is a plan view of the components of FIG. 12, with the components configured for decontamination/purge operation.

After detection of substance(s) by the effluence detection device 76, the detector 76 needs to be decontaminated, with the detected substance purged, before the detector 10 (FIG. 1) is ready for use again. FIG. 13 illustrates the configuration of the system for the purging decontamination operation. The plug 148 is shifted from the port 146 to the port 126 of the fitting 144, and the plug 166 is shifted from the output port 164 to the port 162 of the fitting 158. The heater 170 is turned on to heat the air passing through the system, for example to a temperature of about 177 degrees C. (350 degrees F.), or another suitable temperature. The blower 140 is then turned on. Air is pulled from outside into the loop 154 through the port 146 of the fitting 144. After the air passes through the blower 140 it is heated in the heater 170. The air then is expelled from the loop 154 through the port 164, and into the filter housing 110. The heated air volatizes, and removes traces of the explosives or other substances of interest that had been detected in the effluence detection device 76. This process continues downstream of the filter housing 110, as the heated air passes through the vertical tubes 70 (FIG. 3) and the horizontal tubes 20 (FIG. 1), and out the air intake holes 64 (FIG. 3). The turnstile 26 (FIG. 1) may be rotated during the decontamination and purging process in order to clear traces of substances from all of the vertical tubes 70 and all of the horizontal tubes 20. This removes the traces of explosives or other substances from the detector 10 (FIG. 1).

FIGS. 14-17 illustrate the use of the detector 10 in successive times. At a first time, illustrated in FIG. 14, a first person 200 approaches the rotary gate 12. The first person 200 has not yet entered the fixed sniff area 50.

Figures 14, 15, 16, 17:
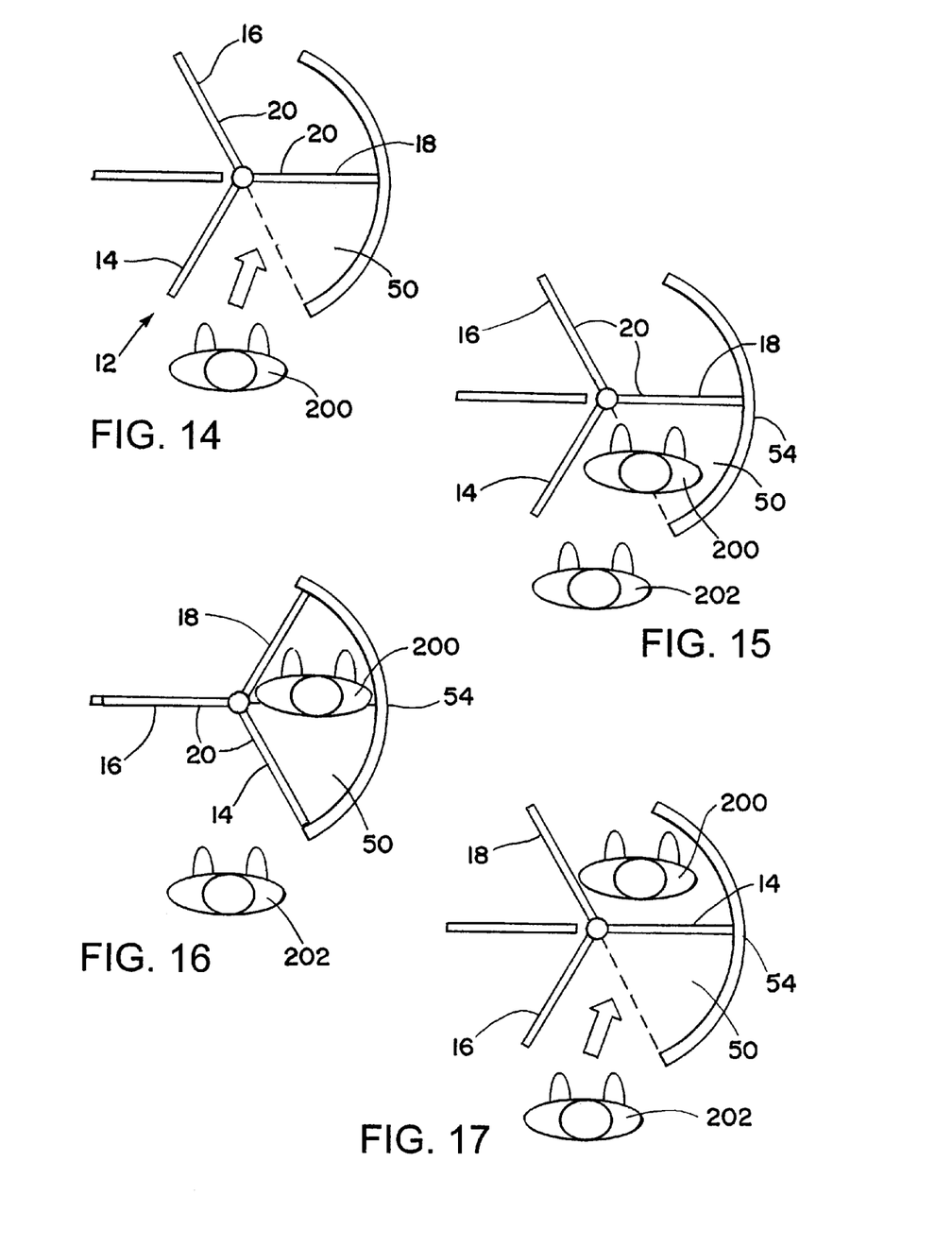
FIG. 14 is a plan view schematically illustrating a first step in the operation of the airborne substance detector of FIG. 1.
FIG. 15 is a plan view schematically illustrating a second step in the operation of the airborne substance detector.
FIG. 16 is a plan view schematically illustrating a third step in the operation of the airborne substance detector.
FIG. 17 is a plan view schematically illustrating a fourth step in the operation of the airborne substance detector.

FIG. 15 illustrates a later time, with the first person 200 having entered the rotary gate 12, and with a second person 202, the next person in line, waiting to enter the rotary gate 12. The rotary gate 12 may be configured to allow only one person at a time to pass through adjacent of the sets 14-18 of the tubes 20.

At the time shown in FIG. 15, the first person has entered the fixed sniff area 50, an area that is necessarily passed through as the rotary gate 12 is passed through. At a later time, illustrated in FIG. 16, the first person 200 has finished passing through the sniff area or zone 50, while the second person 202 has yet to enter the rotary gate 12. The horizontal tubes 20 of the tube set 14 that is following the first person 200 sweep through the fixed sniff area 50, with air being gathered by the air intake holes 64 (FIG. 3) in the tubes 20. The curved stationary shield 54 shields the fixed area 50 from wind or other air currents that might tend to interfere with obtaining a good sample of air from the air just passed through by the first person 200. The manifold 90 (FIG. 7) may limit air gathering to only the tubes 20 that are passing though the fixed area 50—the other tube sets 16 and 18 do not have air drawn through them at this time, nor do they direct air to the effluence detection device 76 (FIG. 6). The gate 12 isolates the first person 200 so that only the air traveled through by the first person is tested for substances.

Finally, FIG. 17 shows the situation after the tubes 20 of the set 14 have passed through the fixed area 50. The first person 200 leaves the rotary gate 12, and the second person 202 enters. The second person is between the tube set 14 and the tube set 16, and the manifold 90 (FIG. 7) may shift to begin pulling air through the tubes 20 of the set 16, to be directed to the effluence detection device 76 (FIG. 7) for testing.

The airborne substance detector 10 has many advantages. The integration into the rotary gate 12 does not slow down the flow of traffic, or alert persons entering the gate 12 about the testing, since the turnstile 26 appears to be a normal gate. A silent alarm may be used when a substance is detected, to maintain the hidden nature of the testing. In addition, the substance detector 10 provides for rapid and sensitive testing, as well as other features. It has built-in decontamination features, and advantageously uses the same fan/blower for both intake of air for testing, and for purging/decontamination.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. An airborne substance detector comprising:
    an air intake movable through a fixed area and rotatable completely around a vertical axis, the air intake including a plurality of tubes, with air intake holes in at least some of the plurality of tubes;
    a fan; and
    an effluence detection device that analyzes for one or more airborne substances;
    wherein the plurality of tubes are arranged in multiple sets of tubes, each set including a series of tubes vertically spaced along a vertical axis, wherein each set is circumferentially spaced from one another about the vertical axis; and
    wherein the fan draws air through the holes and toward the effluence detection device.

2. The airborne substance detector of claim 1, wherein the plurality of tubes include horizontal tubes.

3. The airborne substance detector of claim 1, wherein the plurality of tubes rotate about a central post of the detector.

4. The airborne substance detector of claim 1, wherein the plurality of tubes are parts of a rotary gate that allows pass through of persons in only one direction.

5. The airborne substance detector of claim 4, wherein the plurality of tubes are circumferentially spaced about the central post.

6. The airborne substance detector of claim 2,
    wherein the plurality of tubes include horizontal tubes; and
    wherein the plurality of tubes rotate about a central post of the detector; and
    wherein the horizontal tubes are attached to vertical tubes in the central post.

7. The airborne substance detector of claim 1, wherein at least some of the one or more tubes have porous surfaces.

8. The airborne substance detector of claim 1, wherein the detector includes a rotary gate;

wherein at least part of the air intake is on a turnstile of the rotary gate; and wherein the part of the air intake sweeps through the fixed area as the turnstile turns.

9. The airborne substance detector of claim 1, wherein the air intake is coupled to a manifold that selectively draws in the air through different parts of the air intake.

10. The airborne substance detector of claim 1, wherein the effluence detection device is an explosives effluence detection device for detecting explosive compounds.

11. The airborne substance detector of claim 1, wherein the effluence detection device is a drug sniffer for detecting illegal substances.

12. The airborne substance detector of claim 1, wherein the fan is in a flow loop that includes a heater for heating air that passes through the flow loop.

13. The airborne substance detector of claim 12, wherein the flow loop can be reconfigured to use the fan and the heater for decontamination of the airborne substance detector after the one or more substances are detected.

14. The airborne substance detector of claim 1, further comprising a fixed shield that shields the fixed area from wind or other air currents.

15. The airborne substance detector of claim 14, wherein the shield includes a curved plastic sheet.

16. The airborne substance detector of claim 1, further comprising a space heater directed at part of the fixed area.

17. The airborne substance detector of claim 16, wherein the space heater includes an infrared heater.

18. A method of airborne detection of one or more substances, the method comprising:

detecting the one or more substances using the airborne detector, as a person passes through a fixed area that is within at least part of the airborne detector;

wherein the airborne substance detector includes;

an air intake movable through the fixed area and rotatable completely around a vertical axis, the air intake including a plurality of tubes, with air intake holes in at least some of the plurality of tubes;

a fan; and an effluence detection device that analyzes for one or more airborne substances;

wherein the plurality of tubes are arranged in multiple sets of tubes, each set including a series of tubes vertically spaced along a vertical axis, wherein each set is circumferentially spaced from one another about the vertical axis; and wherein the fan draws air through the holes and toward the effluence detection device.

* * * * *